US00PP28206P2

(12) United States Plant Patent
van den Hoogen

(10) Patent No.: US PP28,206 P2
(45) Date of Patent: Jul. 18, 2017

(54) ***EUPATORIUM* PLANT NAMED 'ALLMELODY'**

(50) Latin Name: *Eupatorium rugosum*
Varietal Denomination: Allmelody

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 14/998,878

(22) Filed: Feb. 25, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — C. A. Whealy

(57) ABSTRACT

A new and distinct cultivar of *Eupatorium* plant named 'Allmelody', characterized by its broadly upright and relatively compact plant habit; moderately vigorous growth habit; freely branching habit; freely flowering habit; green to white-colored inflorescences; strong peduncles; and good container and garden performance.

3 Drawing Sheets

Botanical designation: *Eupatorium rugosum.*
Cultivar denomination: 'ALLMELODY'.

BACKGROUND OF THE INVENTION

The present invention relates to a new and distinct cultivar of *Eupatorium* plant, botanically known as *Eupatorium rugosum* (also known as *Ageratina altissima*), and hereinafter referred to by the name 'Allmelody'.

The new *Eupatorium* plant is a product of a planned breeding program conducted by the Inventor in Cuijk, The Netherlands. The objective of the breeding program is to create new compact *Eupatorium* plants that are suitable as container and garden plants.

The new *Eupatorium* plant originated from an open-pollination in September, 2007 in Cuijk, The Netherlands of a proprietary selection of *Eupatorium rugosum* identified as code number 7-06-1, not patented, as the female, or seed parent with an unknown selection of *Eupatorium rugosum* as the male, or pollen, parent. The new *Eupatorium* plant was discovered and selected by the Inventor as a single flowering plant from within the progeny of the stated open-pollination in a controlled outdoor nursery environment in Cuijk, The Netherlands in September, 2008.

Asexual reproduction of the new *Eupatorium* plant by vegetative cuttings in a controlled outdoor nursery environment in Cuijk, The Netherlands since June, 2009 has shown that the unique features of this new *Eupatorium* plant are stable and reproduced true to type in successive generations.

SUMMARY OF THE INVENTION

Plants of the new *Eupatorium* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Allmelody'. These characteristics in combination distinguish 'Allmelody' as a new and distinct *Eupatorium* plant:

1. Broadly upright and relatively compact plant habit.
2. Moderately vigorous growth habit.
3. Freely branching habit.
4. Freely flowering habit.
5. Green to white-colored inflorescences.
6. Strong peduncles.
7. Good container and garden performance.

Plants of the new *Eupatorium* differ primarily from plants of the female parent selection in plant habit as plants of the female parent selection are more compact and have shorter lateral branches than plants of the female parent selection.

Plants of the new *Eupatorium* can be compared to plants of *Eupatorium rugosum* 'Allmoments', not patented. In side-by-side comparisons, plants of the new *Eupatorium* differ primarily from plants of 'Allmoments' in plant habit as plants of the new *Eupatorium* are more compact and have shorter lateral branches than plants of 'Allmoments'.

BRIEF DESCRIPTION OF THE PHOTOGRAPHS

The accompanying photographs illustrate the overall appearance of the new *Eupatorium* plant showing the colors as true as it is reasonably possible to obtain in colored reproductions of this type. Colors in the photographs may differ slightly from the color values cited in the detailed botanical description which accurately describe the colors of the new *Eupatorium* plant.

The photograph on the first sheet comprises a side perspective view of a typical flowering plant of 'Allmelody' grown in a container.

The photograph on the second sheet is a close-up view of typical leaves of 'Allmelody'.

The photograph on the third sheet is a close-up view of a typical flowering plant of 'Allmelody'.

DETAILED BOTANICAL DESCRIPTION

Plants used for the aforementioned photographs and following description were grown in September in an outdoor nursery in Cuijk, The Netherlands and under cultural practices typical of commercial *Eupatorium* production. During the production of the plants, day temperatures ranged from 13° C. to 26° C. and night temperatures ranged from 6° C. to 16° C. Plants were pinched one time and were four months old when the photographs and description were taken. In the following description, color references are made to The Royal Horticultural Society Colour Chart, 2015 Edition, except where general terms of ordinary dictionary significance are used.

Botanical classification: *Eupatorium rugosum* 'Allmelody'.

Parentage:

*Female parent*.—Proprietary selection of *Eupatorium rugosum* identified as code number 7-06-01, not patented.

*Male parent*.—Unknown selection of *Eupatorium rugosum*, not patented.

Propagation:

*Type cutting*.—Vegetative cuttings.

*Time to initiate roots, summer*.—About 10 to 14 days at temperatures ranging from 12° C. to 30° C.

*Time to produce a rooted young plant, summer*.—About four to six weeks at temperatures ranging from 12° C. to 30° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; broadly upright and relatively compact plant habit; narrow inverted triangle; inflorescences held on strong and upright peduncles; moderately vigorous growth habit.

*Plant height*.—About 43.8 cm.

*Plant diameter or spread*.—About 35 cm.

*Lateral branches*.—Quantity: Freely branching habit; about five main stems per plant each with about seven lateral branches. Length (excluding inflorescence): About 15.8 cm. Diameter: About 3 mm. Internode length: About 4.6 cm. Aspect: Mostly upright. Strength: Very strong. Texture and luster: Densely pubescent; moderately glossy. Color: Close to 143A to 143B.

Leaf description:

*Arrangement*.—Opposite, simple.

*Length*.—About 8 cm.

*Width*.—About 7 cm.

*Shape*.—Broadly ovate to roughly deltoid.

*Apex*.—Acute.

*Base*.—Attenuate.

*Margin*.—Coarsely serrate.

*Texture and luster, upper surface*.—Rugose; pubescence along veins; matte.

*Texture and luster, lower surface*.—Rugose; pubescence along veins; slightly glossy.

*Venation pattern*.—Pinnate.

*Color*.—Developing leaves, upper surface: Close to 143A. Developing leaves, lower surface: Close to 144A. Fully expanded leaves, upper surface: Close to NN137A; venation, close to 147B. Fully expanded leaves, lower surface: Close to 146A; venation, close to 147C.

*Petioles*.—Length: About 2.7 cm. Diameter: About 2.5 mm. Color, upper surface: Close to 146C. Color, lower surface: Close to 144A.

Inflorescence description:

*Appearance and flowering habit*.—Discoid inflorescences arranged in terminal and axillary compound corymbs; inflorescences face mostly upright; freely flowering habit, about 64 corymbs and about 4,000 inflorescences per plant develop during the flowering season; no ray florets have been observed on plants of the new *Eupatorium*.

*Fragrance*.—Very faintly fragrant; sweet, pleasant.

*Time to flower*.—Plants flower continuously from late August to late September in The Netherlands.

*Post-production longevity*.—Inflorescences maintain good substance for about three weeks on the plant; inflorescences persistent.

*Inflorescence buds*.—Height: About 4 mm. Diameter: About 3 cm. Shape: Obovate; apex, flattened. Color: Close to 144B; towards the apex, close to 157C.

*Inflorescence diameter*.—About 1.2 cm.

*Inflorescence height*.—About 1.1 cm.

*Disc diameter*.—About 1.2 cm.

*Receptacle diameter*.—About 1 mm.

*Receptacle height*.—About 0.5 mm.

*Disc florets*.—Quantity and arrangement: About 40 per inflorescence, arranged spirally. Length: About 1 cm. Diameter, apex: About 2 mm. Diameter, base: About 0.5 mm. Shape: Fused in a tube. Apex: Acute. Texture: Smooth, glabrous. Color, immature: Apex and mid-section: Close to 157C to 157D. Base: Close to 150D. Color, mature: Apex: Close to NN155D. Mid-section: Close to NN155C. Base: Close to 157C to 157D.

*Phyllaries*.—Quantity and arrangement: About 15 per inflorescence, arranged in a single whorl. Length: About 5 mm. Width: About 3.5 mm. Shape: Narrowly oblong to lanceolate. Apex: Acute. Base: Cuneate. Margin: Entire. Texture and luster, upper and lower surfaces: Moderately pubescent; matte. Color, upper surface: Close to 144C. Color, lower surface: Close to 144B.

*Peduncles*.—Length: About 8.8 cm. Diameter: About 2.5 mm. Strength: Strong. Aspect: Upright to 35° from vertical. Texture and luster: Densely pubescent; matte. Color: Close to between 143B and 144A.

*Reproductive organs*.—Androecium: Quantity per floret: About five. Anther shape: Lanceolate. Anther length: About 1 mm. Anther color: Close to 199C to 199D. Pollen amount: None observed. Gynoecium: Quantity per floret: One. Pistil length: About 6 mm. Stigma color: Close to NN155D. Style length: About 3.5 mm. Style color: Close to NN155D. Ovary color: Close to 145C. Seeds and fruits: Seed and fruit development have not been observed on plants of the new *Eupatorium*.

Pathogen & pest resistance: Plants of the new *Eupatorium* have not been shown to be resistant to pathogens and pests common to *Eupatorium*.

Garden performance: Plants of the new *Eupatorium* have exhibited good garden performance and to tolerate rain and wind, to be hardy to USDA Zone 5 and to tolerate high temperatures about 35° C.

It is claimed:

1. A new and distinct *Eupatorium* plant named 'Allmelody' as illustrated and described.

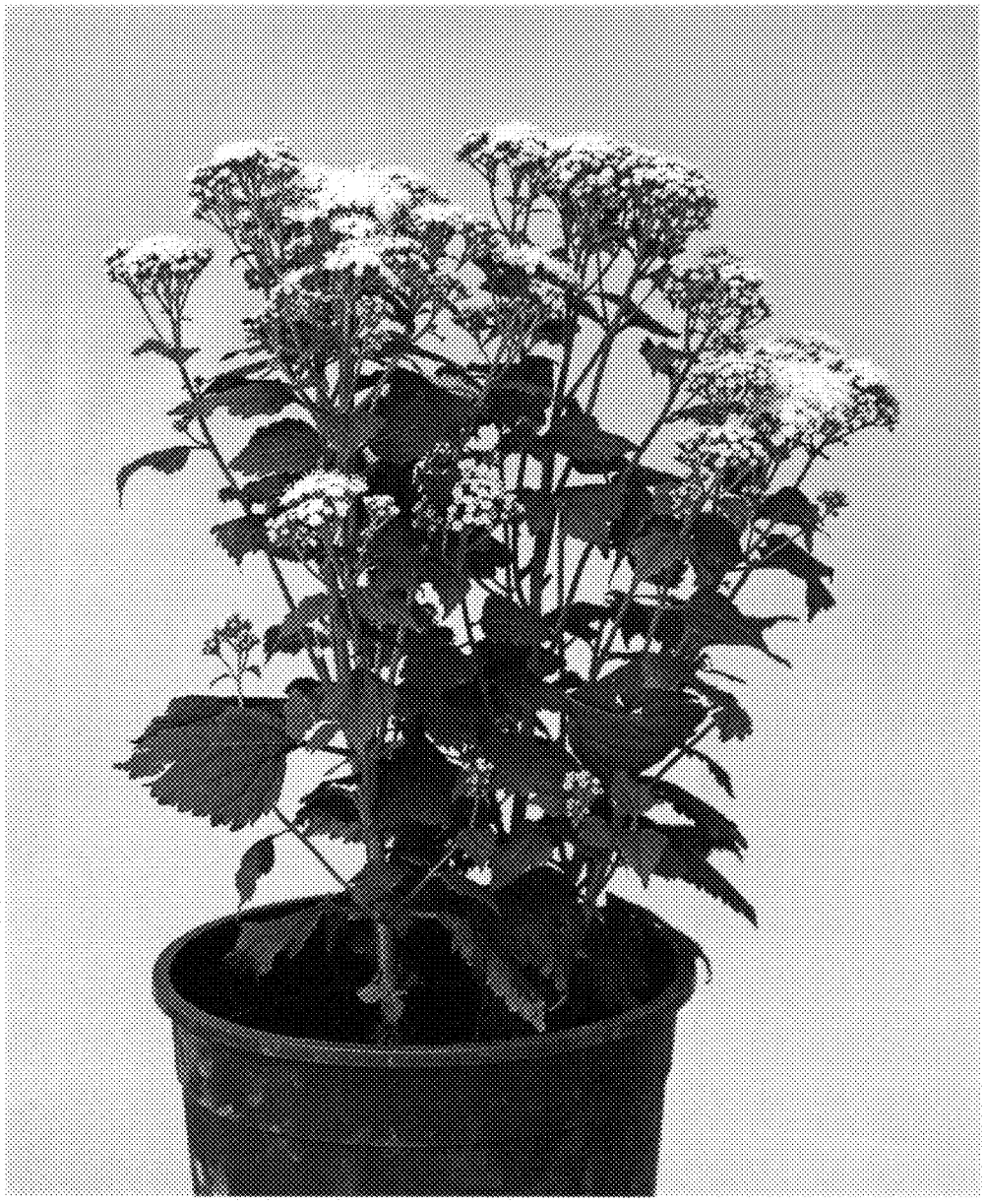

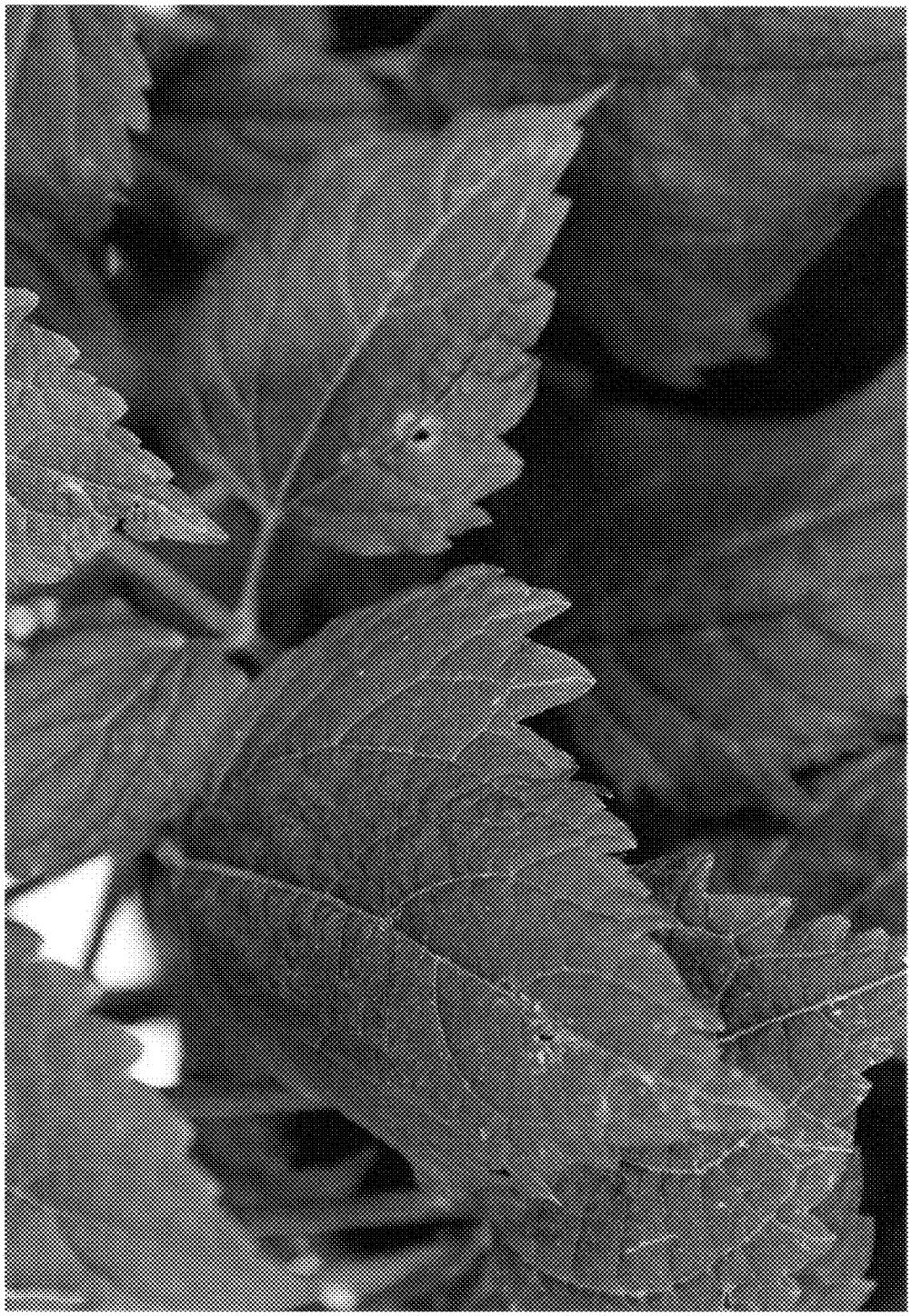

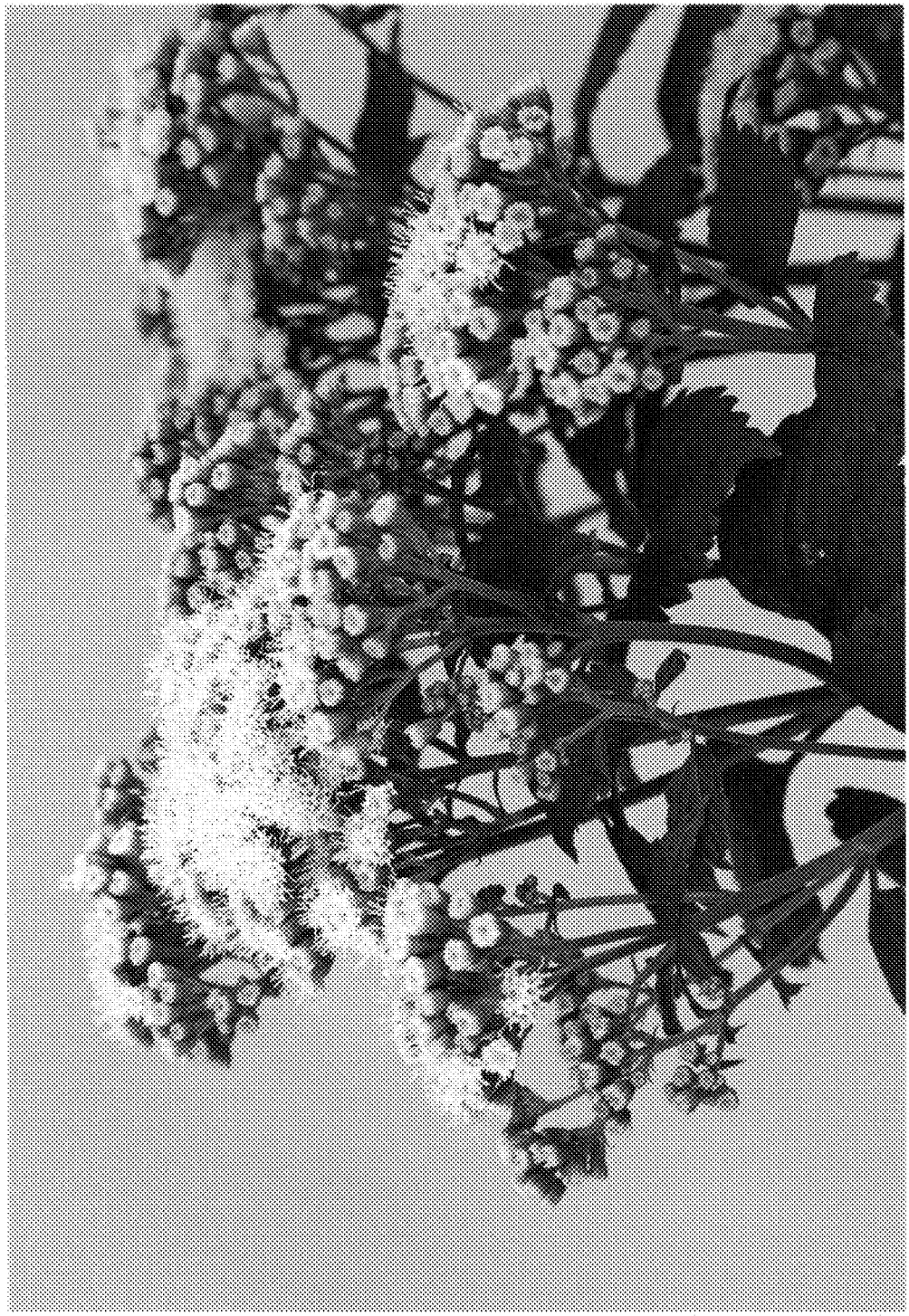

* * * * *